United States Patent
Belfiore et al.

(10) Patent No.: US 8,845,520 B2
(45) Date of Patent: Sep. 30, 2014

(54) SELECTIVE COMPLIANCE WIRE ACTUATED MOBILE PLATFORM, PARTICULARLY FOR ENDOSCOPIC SURGICAL DEVICES

(75) Inventors: Nicola Plo Belfiore, Rome (IT); Massimillano Scaccia, Rome (IT); Francosco Ianniello, Rome (IT); Massimillano Presta, Rome (IT); Luca Perfetti, Rome (IT)

(73) Assignee: Universita' degli Studi di Roma "La Sapienza", Rome (IT)

( * ) Notice: Subject to any disclaimer, the term of this patent is extended or adjusted under 35 U.S.C. 154(b) by 569 days.

(21) Appl. No.: 12/677,975

(22) PCT Filed: Sep. 12, 2008

(86) PCT No.: PCT/IB2008/053698
§ 371 (c)(1), (2), (4) Date: Sep. 2, 2010

(87) PCT Pub. No.: WO2009/034552
PCT Pub. Date: Mar. 19, 2009

(65) Prior Publication Data
US 2011/0028988 A1   Feb. 3, 2011

(30) Foreign Application Priority Data
Sep. 14, 2007 (IT) ............... RM2007A0476

(51) Int. Cl.
*A61B 1/00* (2006.01)
*A61B 19/00* (2006.01)
*A61B 1/008* (2006.01)
*A61B 1/018* (2006.01)

(52) U.S. Cl.
CPC ............. *A61B 1/00098* (2013.01); *A61B 19/26* (2013.01); *A61B 1/008* (2013.01); *A61B 2019/2242* (2013.01); *A61B 2019/2226* (2013.01); *A61B 1/018* (2013.01)

USPC ........... 600/141; 600/139; 600/140; 600/142; 600/146; 600/147; 600/148; 600/149; 600/205; 600/206; 600/207; 600/208; 600/209; 606/1; 606/46; 606/167; 606/170; 606/174; 604/528; 604/95.04; 220/836; 220/837; 220/840; 220/841; 220/842; 220/4.23; 220/4.24; 318/568.12; 74/490.06; 700/254

(58) Field of Classification Search
USPC .......... 600/139–142, 146–149; 220/836, 837, 220/840–842, 4.23, 4.24; 604/528, 95.04; 606/1, 46, 167, 170, 174; 294/34, 57; 74/490.06
See application file for complete search history.

(56) References Cited

U.S. PATENT DOCUMENTS 6,425,177 B1 * 7/2002 Akeel ............................. 29/714
6,817,974 B2 * 11/2004 Cooper et al. ................ 600/142
(Continued)

OTHER PUBLICATIONS
International Search Report for PCT/IB2008/053698, mailed Jul. 10, 2009.

*Primary Examiner* — Matthew J Kasztejna
*Assistant Examiner* — Kevin G Barry, III
(74) *Attorney, Agent, or Firm* — Nixon & Vanderhye, P.C.

(57) ABSTRACT

A wire-operated selective compliance mobile platform (100), in particular for endoscopic surgery devices, obtains a perfect and precise mobility and thus it allows to handle, in the most effective way, the supported instruments, and comprises a mobile surface (1), a connecting base (2) apt to be connected to a flexible tubular duct (4) for endoscopic uses, a plurality of supporting elements (3), apt to permit the motion of said mobile surface (1) relative to said base (2), characterized in that said supporting elements (3) have at least a selective compliance turning pair (31) and a number of joints (32, 34) so as to provide a predetermined number of degrees of freedom to said platform (100), neither determining any over-constraining, nor forcing the system to be deformed in unselected directions, each supporting element (3) being operated by moving means (51, 52) so as to move said mobile surface (1).

17 Claims, 3 Drawing Sheets

(56) References Cited

U.S. PATENT DOCUMENTS

| | | | |
|---|---|---|---|
| 6,858,005 B2 * | 2/2005 | Ohline et al. | 600/141 |
| 8,191,204 B2 * | 6/2012 | Belfiore et al. | 16/225 |
| 2003/0010346 A1 | 1/2003 | Paolitto | |
| 2003/0018323 A1 * | 1/2003 | Wallace et al. | 606/1 |
| 2005/0159732 A1 | 7/2005 | Rosheim | |
| 2005/0216033 A1 * | 9/2005 | Lee et al. | 606/1 |

\* cited by examiner

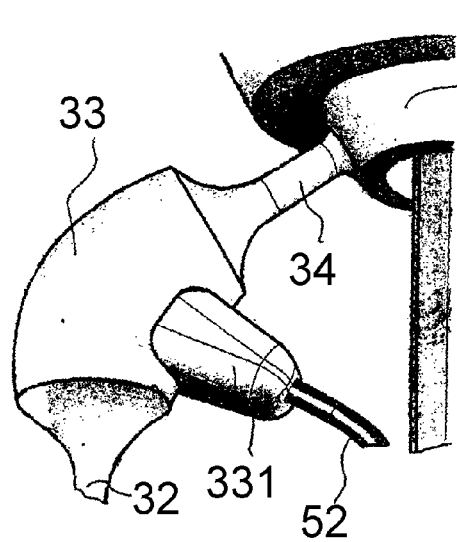
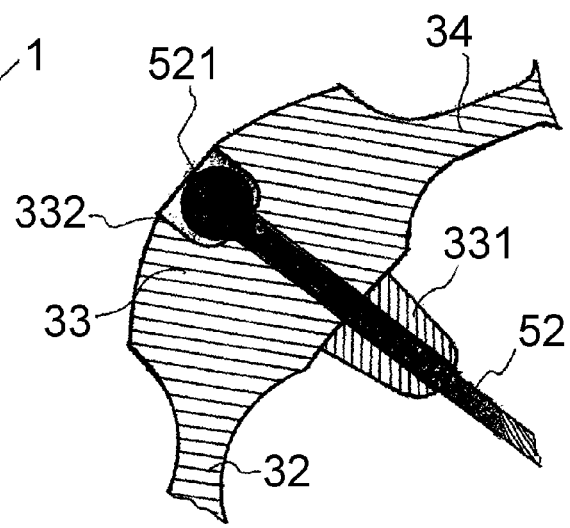
FIG. 2        FIG. 2A
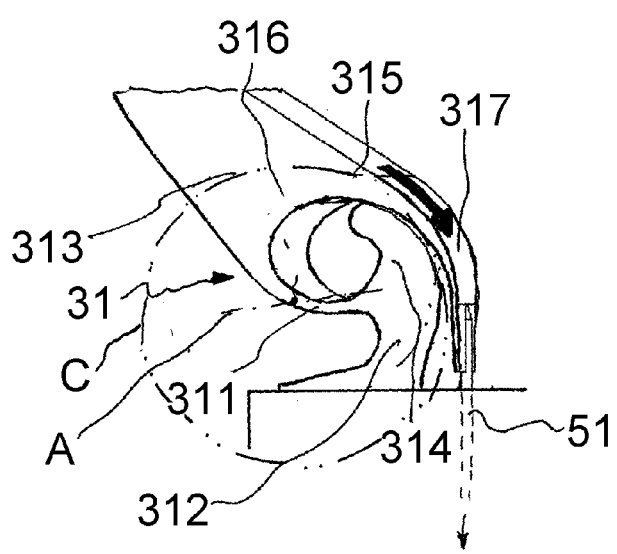
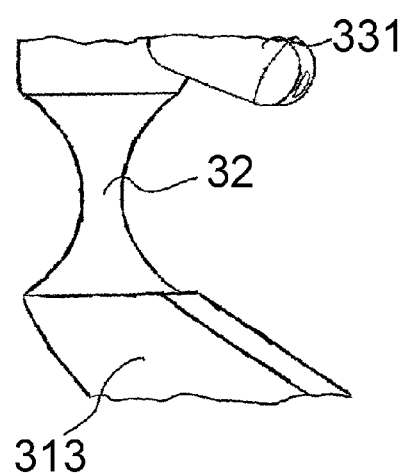
FIG. 3        FIG. 4

SELECTIVE COMPLIANCE WIRE ACTUATED MOBILE PLATFORM, PARTICULARLY FOR ENDOSCOPIC SURGICAL DEVICES

This application is the U.S. national phase of International Application No. PCT/IB2008/053698, filed 12 Sep. 2008, which designated the U.S. and claims priority to Italian Patent Application No. RM2007A000476, filed 14 Sep. 2007, the entire contents of each of which are hereby incorporated by reference.

The present invention refers to a wire-operated selective compliance mobile platform, for example designed for being used in endoscopic surgery devices.

Endoscopic surgery devices are instruments designed for making inspections of body cavities (natural and not) and for performing operations inside them.

These instruments are typically provided with a vision system, usually equipped with a high resolution CCD sensor placed at the end of the instrument working inside the cavity, and then displaying what observed on a monitor. If used in surgery, these instruments could be provided with several tools (forceps, scissors, electrotomes, etc., according to the required operation) inserted within an appropriate operative channel for operating at the observed region.

It is evident that these instruments should have extremely small dimensions in order to be used in corporal cavities without being too invasive. Nevertheless, at the same time, their control should be easy and precise, since the surgeon needs to move the end of the endoscope having the vision sensor and/or the surgical tools, in order to precisely reach the portion to be examined or to be operated.

Therefore, mobile platforms for allowing the motion of sensors and tools are used at the end of the instrument. It is desirable that such motion not only is the more complete as possible within the available space, but also, as said before, it is precise, repeatable, and easily operated, the overall system being made of extremely reduced dimensions.

As a consequence, the manufacturing of a surgical instrument with these features is technically rather difficult since they require, among other aspects, high manufacturing costs. Moreover, instruments made according to the state of the art do not always reveal to be perfectly efficient and practical during their use.

In order to try to overcome these problems, endoscopic instruments wherein the platform has a mobility provided by selective compliant joints have been recently developed. These joints have the peculiarity of being made as a single body, and to have a narrow connecting section, characterized by dimensions allowing a great deformability in one or more default directions, and a great stiffness in the other directions.

Therefore, this characteristic allows to have kinematic pairs made as a single body and, accordingly, allows to make surgical instruments particularly compact, at least theoretically.

Nevertheless, instruments having mobility by selective compliance hitherto known to the art do not guarantee enough easiness of motion and precision, since the geometry and the choice of the joint used therein do not guarantee a perfect control of the structure. In fact, the ideal condition of infinite stiffness in all directions except the desired one is not actually achieved and, as a consequence, structures so far developed have a certain lability and they are not suitable for a medical use or for other uses requiring precision. In fact, it should be noted that analogous problems could be found even in other fields of use, such, e.g., uses for aerospace engineering wherein the absence of atmosphere causes problems comparable to the one previously described, although working on a different scale. Moreover, in this case, one of the greatest difficulty consists of the need to work without lubrication in the mechanical pairs and without needing particular maintenance. As a consequence, even in this case the use of components having a mobility by selective compliance, guarantying at the same time a high precision in the movements, is particularly desirable.

Hence, the technical problem underlying the present invention is to provide a device for endoscopic surgery and, more in general, for precision uses, allowing to overcome the drawbacks mentioned above with reference to the known art.

Such a problem is solved by the wire-operated selective compliant mobile platform according to claim 1 and by the surgical device according to claim 14.

The present invention provides several relevant advantages. The main advantage lies in that the selective compliance platform according to the present invention guarantees a perfect and precise mobility and thus it allows to operate the supported instruments in the most effective way. Moreover, the structure can be easily and cheaply manufactured, even if it is characterized by small dimensions and by a great structural sturdiness. Finally, the platform does not need any lubrication or any particular maintenance and, therefore, it is particularly suitable to be used in problematic environmental conditions, such the ones related to aerospace uses.

Other advantages, features and the operation modes of the present invention will be made apparent from the following detailed description of some embodiments thereof, given by way of a non-limiting example. Reference will be made to the figures of the annexed drawings, wherein:

FIGS. 2 and 2A are a perspective view and a sectional side view, respectively, of a supporting element of the platform of FIG. 1, provided with the moving means of FIG. 1A;

FIG. 3 is a perspective view of a selective compliance turning pair, detail of the supporting element of the platform of FIG. 1;

FIG. 4 is a perspective view of a selective compliance spherical joint, detail of the supporting element of the platform of FIG. 1.

Figure 1:
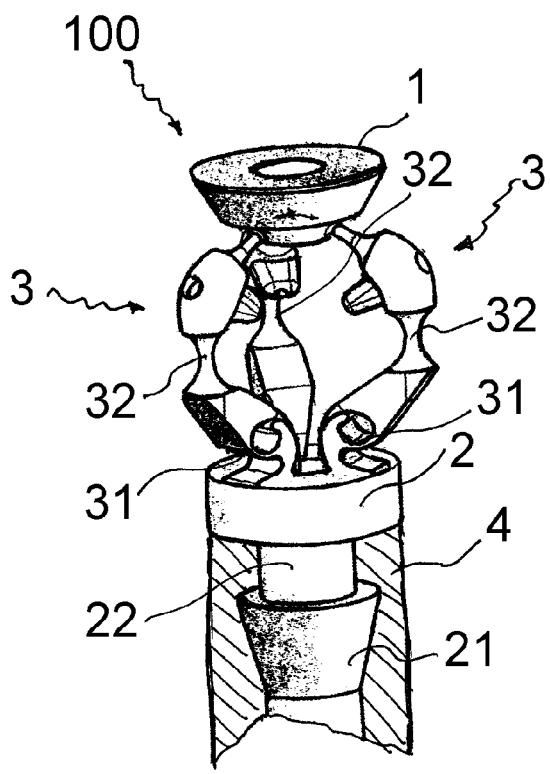
FIG. 1 is a perspective view of wire-operated selective compliant mobile platform according to the present invention.
Figure 5:
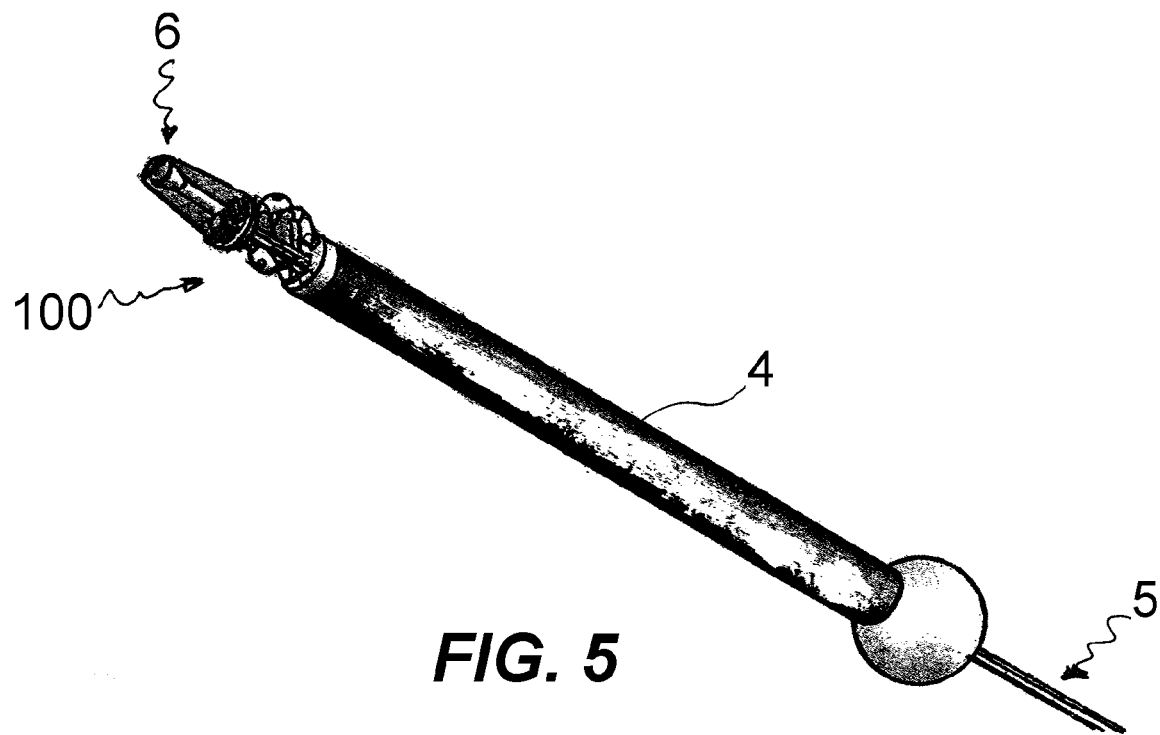
FIGS. 5 and 5A are a perspective view and a detail view thereof, respectively, of a mini-invasive surgical device comprising the platform of FIG. 1.
Figure 5A:
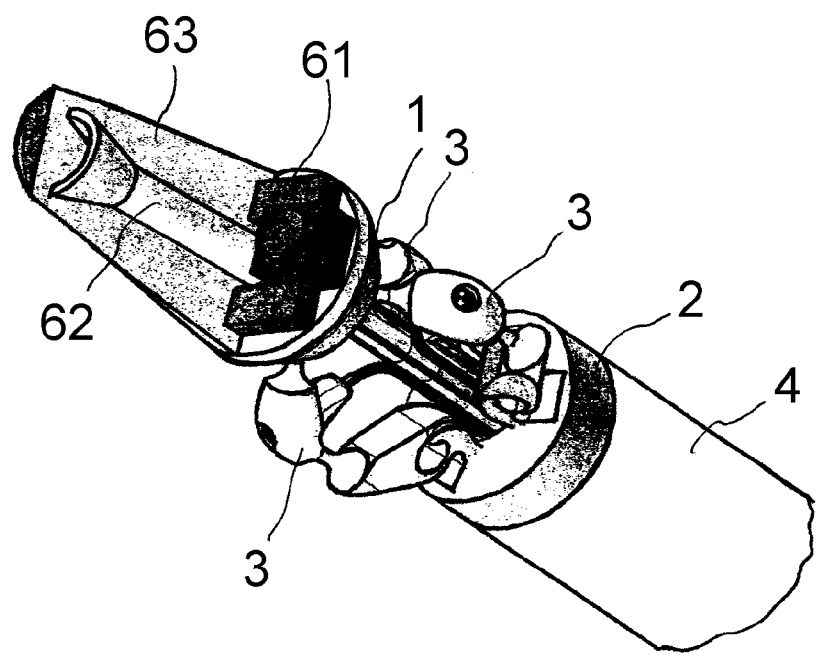

With reference initially to FIG. 1, a wire-operated selective compliance mobile platform is generically shown with the number 100 and is connected to a flexible tubular duct 4 for endoscopic, surgical, therapeutic or diagnostic uses. As it will be seen in the following, and as shown in FIGS. 5 and 5A, the platform 100 is designed for supporting surgical means 6 normally used during endoscopic surgical operations, such as vision systems, forceps, scissors, cannulae, electrotomes etc. Alternatively, an instrument for a therapeutic or diagnostic use could be joined to the platform 100.

Analogously, the system could be used for precision applications or in adverse environments such as, e.g., for operating in orbiting satellites. It is evident that, in these cases, different structural dimensions and features will be required. Anyhow these differences could be deduced by a person skilled in the art according to the following description relating to the present embodiment.

Then, with reference to the example of FIG. 1, the platform 100 substantially comprises a mobile surface 1, wherein the above mentioned surgical means 6 will be housed, a connecting base 2 with the tubular duct 4, and a plurality of supporting elements 3, allowing a mobile connection between base 2 and mobile surface 1.

It should be noted that the mobile base has connecting means allowing a removable connection of the platform 100 with the tubular duct 4, so that platform 100 and tubular duct 4 can be easily assembled and, in case, substituted, nevertheless keeping the components directed to control and operate the platform, as it will be seen in details in the following, with a remarkable economic advantage.

This removable connecting means can be made, e.g., by a conical ring 21 connected to a reduced section collar 22 inserted interlocking on the tubular duct 4. In any case, a pneumatic or hydraulic locking system placed at the base 2 can be also provided, for stabilizing the position of the platform and making the operation safer.

Figure 1A:
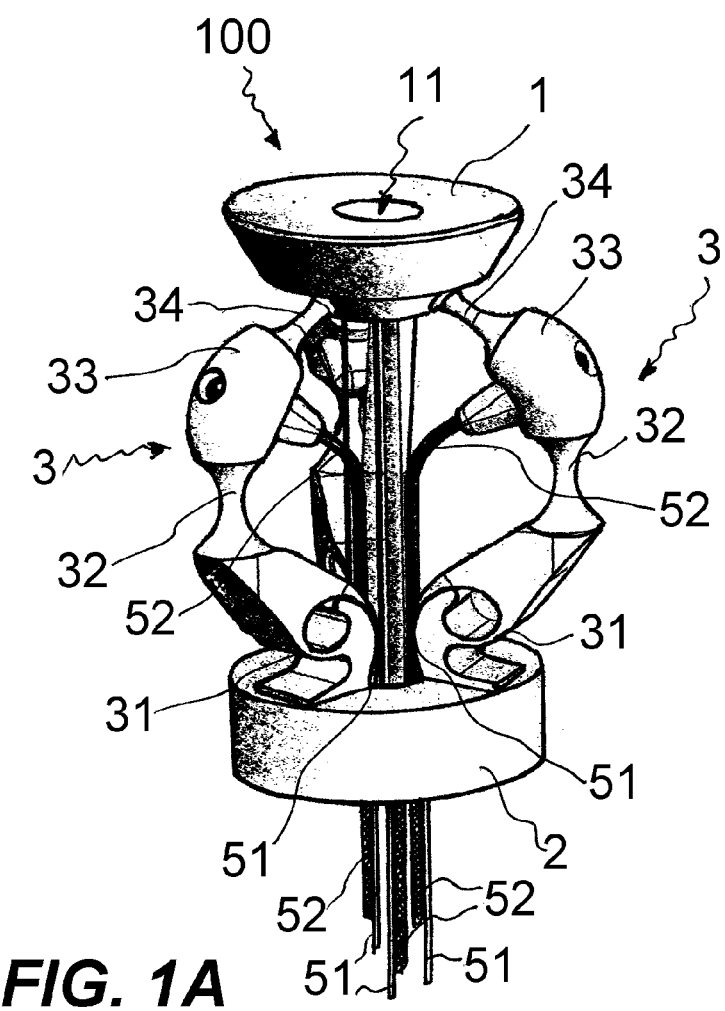
FIG. 1A is a perspective view of the platform of FIG. 1 and moving means thereof.

With reference now to FIG. 1A, the supporting elements 3 provide mobility in space to the mobile surface 1, and are operated by moving means 5, made by actuator wires 51, 52 running inside the tubular duct 4, for allowing to remotely control and operate the platform. The use of moving means 5 made by actuator wires 51, 52 is anyhow known to the person skilled in the art and, therefore, it will not be described in further details.

In the present embodiment, the supporting elements 3 are elongated and, in particular, are in number equal to three.

Each supporting element 3 has selective compliance portions providing the mobile surface 1 the required degrees of freedom. With reference to above described supporting elements, which are in a number equal to three, the mobile base 1 could be operated in space by using an appropriate kinematic configuration, since it is provided of six degrees of freedom and of the same number of actuator wires 51, 52.

This characteristic is particularly advantageous since it allows an extremely practical manufacturing of the platform, since each of the three supporting elements 3 of the present embodiment could be made separately, as a single body, and, thus, the assembling could be simply made between base 2, surface 1 and elements 3.

The mobility by selective compliance advantageously derives from the combined presence of turning pairs 31 and of first and second joints 32 and 34. In particular, in the present embodiment, each supporting element 3 has a selective compliance turning pair 31, a first selective compliance joint 32, the kinematic characteristic thereof being described in the following, and a second selective compliance joint 34, substantially of the spherical kind.

Turning pairs 31 allow a degree of freedom and act as a precision elastic hinge, by the configuration that will be described in the following.

Joints 32 and 34 are shaped as solid of revolution with the smaller section at the middle of the symmetry segment and with a further symmetry to the smaller section itself. In further details, joints 32 are made such that the relative motion between the connected parts has selectively two degrees of freedom, deriving only from the bending of the joint in any plane passing through the axis of symmetry. These joints 32 have approximately the function of elastic cardan joints, being the equivalent cardan centre placed at the barycentre of elastic weights of the joint itself.

The second joints 34, similar to the first joints 32 but provided with a even more reduced section, allow the torsion about the axis of symmetry besides the bending inside any plane passing through said axis. Accordingly, joints 34 substantially have the function of spherical elastic joints, being the equivalent centre of the spherical kinematic pair placed at the barycentre of elastic weights of the joint itself.

This described combination allows to obtain a great maneuverability of the mobile surface 1, and moreover, as it will be seen in the following, it allows a great precision in the movements of the structure thanks to the characteristics of the kinematic pairs.

The moving means 5 acts on the turning pairs and on the other joints so that they provide the mobility thereof and, in particular, are connected to first actuator wires 51 and to second actuator wires 52, according to conditions that will be described in the following.

Each actuator wire 51 operates almost exclusively the rotation of the corresponding elastic turning pair 31. Each wire 52 operates prevalently the bending of the corresponding joint 32. Nevertheless, the difficulties in achieving the equilibrium of the elastic system is such that the tension forces affects each other. Therefore the global configuration of the platform will be defined by the whole set of forces applied to all the wires, since it depends on the interaction between the applied forces and on the elasticity of joints.

The number of actuators could correspond to the number of degrees of freedom conferred to the mobile surface 1. Anyhow, a redundant number of actuator wires could be used for reducing or eliminating any possible hysteresis or elastic recovery.

Always with reference to FIG. 1A, the supporting elements 3 further comprise a docking portion 33 docking to the actuator wire 52 joining the joints 32 and 34 at opposed ends thereof.

In particular, with reference to FIGS. 2 and 2A, the actuator wires 52, acting on the selective compliance joints 32 and 34, have widened end 521 housed inside a seat 332. This feature allows an easy assembling of the platform. Moreover, in order to improve the maneuverability of the mobile surface 1, the docking portion 33 is provided with a collar 331 inside which the actuator wire 52 is partially housed. It should be noted that the structural solutions used for placing the actuator wires, allow to minimize the stress at the ends of the wires, on equal terms of displacements.

With reference now to FIG. 3, a selective compliance turning pair 31 could be advantageously made using a compliant connecting section 311 joining two parts 312 and 313 mobile therebetween.

In the present embodiment, the turning pair 31 have the purpose of providing the rotation movement by the selective compliance of the connecting section 311, about the axis shown with the letter A in FIG. 3. In particular, experimentally it has been observed that a possible design for the connecting section 311 for having a turning pair and guarantying a rotation between the first and the second parts 312 and 313, requires to place the center of relative rotation 316 of the first and second part 312, 313 substantially at the barycenter of elastic weights of the connecting section 311.

Therefore, the axis of rotation A will be passing through the center of rotation 316 and perpendicular to a plane of development of the hinge.

Always with reference to FIG. 3, each part 312, 313 has a first and a second extension 314, 315, respectively, comprising respective surfaces conjugated therebetween.

More precisely, the above mentioned surfaces will be facing therebetween and, as it will be seen in further detail in the following, they will remain as such during the movements of the hinge.

In fact, according to a preferred embodiment, these surfaces develop substantially along arcs of a circle C having the centre corresponding to the centre of mutual rotation 316 defined by the barycenter of elastic weights, and previously described. Accordingly, during the movement between the parts 314, 315, provided by the selective compliance of the connecting element 311, said surfaces will slide one relative the other remaining adjacent therebetween and therefore defining a rotation substantially about the default axis of rotation A, the latter passing through the centre 316 of the circle C.

Then, it should be noted that the rotary movement about the axis A not only is determined by the characteristic of selective compliance of the connecting element 311, as described above, but also it is driven by the shape coupling between the surfaces sliding the one on the other and following a predetermined path, defined by the circle C.

Therefore, the movement provided by this turning pair will be precise and repeatable, characteristic particularly desirable for uses in endoscopic surgery or for other precision uses.

The turning pair 31 is moved by the actuator wire 51 connected by the prolongation 317 of the extension 315.

Accordingly, e.g., a consequent rotation of the pair 31 about axis A will be prevalently obtained by pulling the actuator wire 51 even if, as previously described, a partial motion also of the other joints 32 and 34 will take place for the kinematic complexity of the structure.

Then, with reference to FIG. 4, the supporting element 3 is formed by the joints 32 and 34 made by a narrow section portion.

In particular, the second joint 34, having a higher compliance than the first joint 32, is connected to and supports the mobile surface 1. In turn, the joint 32 is connected to the part 313 of the turning pair 31.

By using three supporting elements 3 it will be possible to operate the platform by providing two tensions to wires 52 and 51, for each supporting element. The six tensions, that could be independently chosen, will determine the positioning of the mobile platform, having six degrees of freedom distinctive of a body in the space, according to the assigned structure.

If the operations to be performed are particularly easy, it possible to limit the number of wires to be actuated. In this case, the equilibrium of the system will be based on the natural elastic equilibrium thereof. E.g., it will anyhow possible to move the platform by controlling a single wire, but, in this case, the former will have only a limited number of configurations.

Moreover, it should be comprised that, according to the principles above described, even embodiments using a greater number of supporting elements 3 could be also considered.

In the case of four supporting elements are used, it will be appropriate to use four wires 51 and two wires 52.

In the case of five supporting elements are used, it will be appropriate to use five wires 51 and one wire 52.

In the case of six supporting elements, it will be appropriate to use exclusively six first actuator wires 51. This solution could be particularly advantageous since only first actuator wires connected to the turning pairs are used and, therefore, they are placed in a more proximal position to the tubular duct 4, thus allowing an improved protection of the structure.

As a further alternative, it is possible to vary in a combinatorial way the position of the turning pairs 31 and of the joints 32 and 34 in the supporting elements.

An alternative solution could, e.g., envisage the use of four supporting elements 3, two of them comprising two turning pairs 31 each and a second joint 34, and two comprising a turning pair 31 each and two second joints 34. Again in alternative, six supporting elements 3, two of them as in the example of FIG. 1, and the other four as the preceding example.

The available combinations for the different uses will derive from the degrees of constraint of each elastic joint used, which should give the platform on the whole the required degree of mobility (typically, six in the space).

Thus, in general, the selective compliance turning pair 31, being present at least in one supporting element 3, and the joints 32 and/or 34, present in a variable number according to the adopted embodiment and to the required degrees of freedom, give to the platform 100 a substantially predetermined number of degrees of freedom, neither determining any overconstraining nor forcing the system to be excessively deformed in unselected directions, eliminating at most the "parasitic" stiffness.

With the term parasitic stiffness it is meant stiffness in selective compliance mechanism in directions along which there should be an ideal situation of perfect compliance, in order to have a perfect deformability of the mechanism in the desired directions.

Therefore, in other words, it is to be intended that the motion of the platform is provided only by the deformation of the selective compliance components, precisely thanks to the combined use of turning pairs and of cardan and/or spherical joints, the system being substantially not subjected to other deformations, that would be just caused by the presence of the above mentioned parasitic stiffness. This characteristic allows to operate with the greatest precision, since the motion would not be still controlled if the system has been forced to deformations in unselected directions, and to guarantee the greatest durability thereof.

Therefore, the supporting elements 3 are operated by one or more actuator wires, acting on the turning pairs and on the first and second joints, so that the mobile base 1 is moved according to the just described operations. In particular, the motion will be selected according to the actuator wire used. E.g., if the first wires 51 are kept still and if the second wires 52 are simultaneously moved, a translation of the mobile base 1 along the axial direction defined by the tubular duct 4 will be obtained.

Then, with reference to FIGS. 5 and 5A, a surgical endoscopic device comprising the platform 100 according to the present invention is shown. The mobile surface 1 supports the surgical means 6 that can vary according to the type of operation required.

In general, vision means 61 will be provided, allowing the observation of the corporal cavity wherein the device is inserted.

Moreover, a communication duct 62 is defined, allowing the communication between outside the surgical device and the region to be operated.

In particular, as could be seen in FIG. 1A, the mobile surface 1 and the base 2 are also provided with an opening, shown with the reference 11 for the surface 1, and connecting the duct 62 with the tubular duct 4.

Always with reference to FIG. 5A, it should be also noted that the surgical device comprises a shaped surface 63 allowing to act as a guiding element inside the cavity during the use of the device.

Examples of surgical means that can be used in the device according to the present invention comprise electrotomes, electro-coagulation devices, devices for suturing, scissors and forceps, in particular provided with a mobility by selective compliance, cannulae for the flow of excised tissue in physiological solution or other fluids, laser conducting fibers, visible, infrared or ultraviolet spectrum lightning leds.

Incidentally, the head portion of the device, thus consisting of the platform 100 with integrated surgical means 6, has dimensions—variable according to the medical requirements—from about 20 mm to 2 mm and less, also according to the diameter of the flexible tubular duct.

Therefore, the surgical device is particularly versatile and, always as an example, could be used in surgical operations in different specialities, endoscopic observations, biopsies, targeted administering of medicines, targeted administering of capsules with nano- or micro-technological devices, biomedical measuring (fluximetry, pressure, etc.). Finally, it should be noted that in the present example of use, the platform according to the present invention is particularly useful since it could be easily substituted after any operation, keeping the moving means, with an evident economical saving.

The present invention has hereto been described with reference to preferred embodiments thereof. It is understood that there could be other embodiments referable to the same inventive kernel, all falling within the protective scope of the claims set forth hereinafter.

The invention claimed is:

1. A cable-operated selective compliance mobile platform for endoscopic surgery devices, comprising:
    a mobile surface;
    a connecting base apt to be connected to a flexible tubular duct for endoscopic uses; and
    a plurality of supporting elements involving at least one elastic weight, connecting said mobile surface and said connecting base to each other, each of the supporting elements being made as a single body and having:
    at least one selective compliance portion defining a joint shaped as a solid of revolution with a smaller middle section, made such that a relative motion between connected parts has selectively two degrees of freedom deriving only from the bending of the joint in any plane passing through an axis of symmetry thereof, said joints acting as elastic cardan joints, an equivalent cardan centre thereof being placed at a barycentre of the elastic weights of the joint;
    at least a selective compliance turning pair comprising a compliant connecting section joining two parts involving said elastic weights and said mobile surface therebetween, providing a rotation movement by the compliant connecting section about an axis at the barycentre of said elastic weights,
    so as to provide a predetermined number of degrees of freedom to said platform,
    neither determining any over-constraining, nor forcing the system to be deformed in unselected directions, each supporting element being operated by a moving structure so as to move said mobile surface.

2. The cable-operated selective compliance mobile platform according to claim 1, wherein said supporting elements are in a number equal to three, each of them comprising one selective compliance turning pair and a first and a second selective compliance joint.

3. The cable-operated selective compliance mobile platform according to claim 1, wherein said supporting elements are in a number equal to six, each of them comprising one selective compliance turning pair and at least one selective compliance joint, wherein said moving structure is connected to said turning pairs.

4. The cable-operated selective compliance mobile platform according to claim 1, wherein said at least one turning pair has a first and a second extension, respectively, said extensions comprising respective conjugate surfaces, in a such way that said surfaces slide one relative the other, remaining adjacent therebetween and defining a rotation substantially about a default axis of rotation.

5. The cable-operated selective compliance mobile platform according to claim 1, wherein said at least one selective compliance joint comprises a narrow section portion apt to provide said selective compliance.

6. The cable-operated selective compliance mobile platform according to claim 1, wherein each supporting element is apt to be operated by actuator cables, connected to said turning pairs and said joints, respectively.

7. The cable-operated selective compliance mobile platform according to claim 1, comprising connecting structure to said flexible tubular duct.

8. The cable-operated selective compliance mobile platform according to claim 2, wherein said second joints have a greater compliance than said first joints.

9. The cable-operated selective compliance mobile platform according to claim 2, wherein said first joints substantially behave as cardan joints and said second joints substantially behave as spherical joints.

10. The cable-operated selective compliance mobile platform according to claim 2, wherein said first joints and said second joints are connected to a docking portion, onto which said moving structure operates.

11. The cable-operated selective compliance mobile platform according to claim 1, wherein said second spherical joints are connected to said mobile surface.

12. A surgical device comprising a flexible tubular duct, a cable-operated selective compliance mobile platform and a surgical device, said cable-operated mobile platform comprising:
    a mobile surface;
    a connecting base apt to be connected to a flexible tubular duct for endoscopic uses; and
    a plurality of supporting elements involving at least one elastic weight, connecting said mobile surface and said connecting base to each other, each of the supporting elements being made as a single body and having:
    at least one selective compliance portion defining a joint shaped as a solid of revolution with a smaller middle section, made such that a relative motion between connected parts has selectively two degrees of freedom deriving only from the bending of the joint in any plane passing through an axis of symmetry thereof, said joints acting as elastic cardan joints, an equivalent cardan centre thereof being placed at a barycentre of the elastic weights of the joint;
    at least a selective compliance turning pair comprising a compliant connecting section joining two parts involving said elastic weights and said mobile surface therebetween, providing a rotation movement by the compliant connecting section about an axis at the barycentre of said elastic weights,
    so as to provide a predetermined number of degrees of freedom to said platform,
    neither determining any over-constraining, nor forcing the system to be deformed in unselected directions, each supporting element being operated by a moving structure so as to move said mobile surface.

13. The surgical device according to claim 12, wherein said surgical device comprises a vision system.

14. The surgical device according to claim 12, wherein said platform is removably connected to said flexible duct.

15. The surgical device according to claim 12, wherein said at least one turning pair has a first and a second extension, respectively, said extensions comprising respective conjugate surfaces, in a such way that said surfaces slide one relative the other, remaining adjacent therebetween and defining a rotation substantially about a default axis of rotation.

16. The surgical device according to claim 12, wherein said at least one joint comprise a narrow section portion apt to provide said selective compliance.

17. The surgical device according to claim 12, wherein each supporting element is apt to be operated by actuator cables, connected to said turning pairs and said joints, respectively.

* * * * *